(12) United States Patent
Hakansson et al.

(10) Patent No.: US 8,223,983 B2
(45) Date of Patent: Jul. 17, 2012

(54) FITTING AND VERIFICATION PROCEDURE FOR DIRECT BONE CONDUCTION HEARING DEVICES

(75) Inventors: Bo Hakansson, Gothenburg (SE); William Hodgetts, Edmonton (CA)

(73) Assignee: Osseofon AB, Gothenburg (SE)

( * ) Notice: Subject to any disclaimer, the term of this patent is extended or adjusted under 35 U.S.C. 154(b) by 761 days.

(21) Appl. No.: 12/323,842

(22) Filed: Nov. 26, 2008

(65) Prior Publication Data
US 2009/0136050 A1  May 28, 2009

(30) Foreign Application Priority Data

Nov. 28, 2007  (SE) .................................. 0702629-7
Dec. 21, 2007  (SE) .................................. 0702894-7

(51) Int. Cl.
*H04R 29/00*  (2006.01)
(52) U.S. Cl. ......................................... 381/60; 381/326
(58) Field of Classification Search ................. 381/60, 381/326, 151, 380; 600/25, 559; 607/55, 607/57
See application file for complete search history.

(56) References Cited

U.S. PATENT DOCUMENTS

| | | | |
|---|---|---|---|
| 5,771,298 A * | 6/1998 | Davis et al. ...................... 381/60 |
| 6,157,861 A | 12/2000 | Faltys et al. | |
| 6,792,114 B1 | 9/2004 | Kates et al. | |
| 2004/0152946 A1 | 8/2004 | Franck | |
| 2007/0258609 A1 | 11/2007 | Steinbuss | |
| 2010/0041940 A1 * | 2/2010 | Hillbratt et al. ................. 600/25 |

FOREIGN PATENT DOCUMENTS

WO  9836711  8/1998

OTHER PUBLICATIONS

Jin et al., "Individualization in Spatial-Audio Coding" 2003 IEEE Workshop on Applications of Signal Processing to Audio and Acoustics, Oct. 19-22 2003, New Paltz, NY, pp. 213-216.

* cited by examiner

*Primary Examiner* — Evan Pert
*Assistant Examiner* — Scott Stowe
(74) *Attorney, Agent, or Firm* — Gesmer Updegrove LLP

(57) ABSTRACT

The present invention relates to a method for fitting and verification of direct bone conduction hearing devices to a patient, wherein a. in a first step the hearing threshold and loudness discomfort levels are measured directly on a titanium implant of a patient, b. in a second step these hearing threshold and loudness discomfort levels are converted to equivalent force thresholds ($F_{HT}$) and loudness discomfort levels ($F_{LDL}$) on an artificial skull force measuring device, c. in a final step the output force levels of the direct bone conduction hearing device is measured in a free sound field with the device attached to the said artificial skull force measuring device and compared to the $F_{HT}$ and the $F_{LDL}$ as the base for final adjustments of the device.

12 Claims, 1 Drawing Sheet

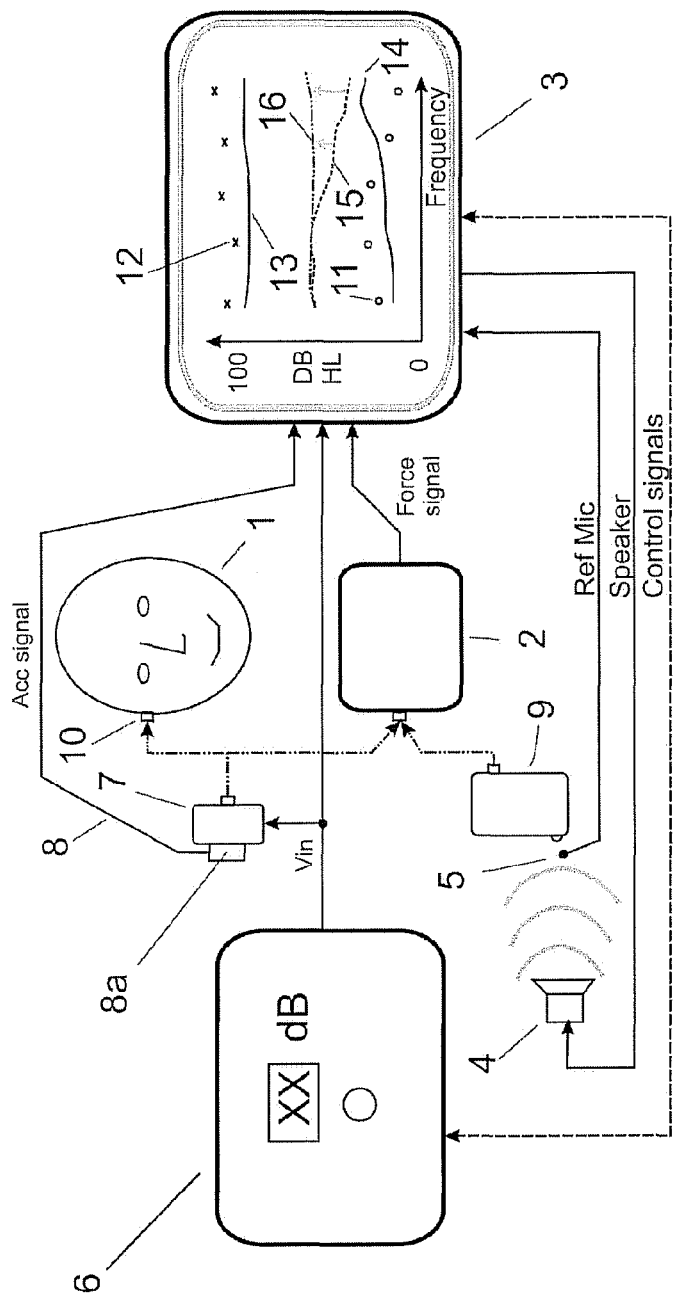
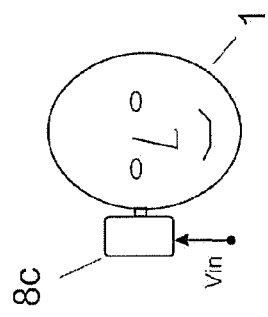
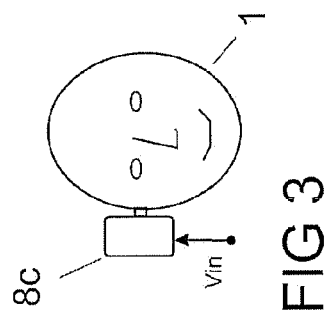
FIG 1
FIG 2
FIG 3

FITTING AND VERIFICATION PROCEDURE FOR DIRECT BONE CONDUCTION HEARING DEVICES

PRIORITY INFORMATION

This application claims priority to Swedish Application No. 070629-7, filed on Nov. 28, 2007 and Swedish Application No. 0702894-7, filed on Dec. 21, 2007, both applications are incorporated herein by reference in their entireties.

DESCRIPTION

1. Technical Field

The present innovation is intended as a method to improve the fitting procedure in direct bone conduction hearing devices. Direct bone conduction devices are used most frequently in patients who cannot use conventional air conduction devices because of chronic external ear or middle ear infections or in patients with malformations.

2. Background to the Invention

A main goal for verifying the appropriateness of any hearing aid fitting should be to match, as closely as possible, the amplification characteristics of the hearing aid to the unique auditory characteristics of the hearing impaired listener. Each hearing impaired listener will have a unique dynamic range of hearing. The dynamic range represents the difference, in decibels, between the softest sound a person can hear at each frequency (Hearing thresholds) and the loudest sound that they will tolerate at each frequency (Loudness Discomfort Levels; LDLs). Hearing aid clinicians typically apply some form of fitting rationale or prescriptive algorithm in order to ensure that the aided frequency response (output) of the hearing aid is set in such a way as to maximize the audibility of speech sounds regardless of the input level to the patient.

In order to directly verify the relationship between the hearing aid output response and the dynamic range of hearing, all parameters (thresholds, LDLs and hearing aid output) should be converted to the same units with a common reference point. In the case of air conduction hearing aids, the thresholds, LDLs and hearing aid responses are typically converted to sound pressure level (SPL) units and the common reference point is the ear canal. One of two approaches is applied to do this: (1) real ear in-situ and (2) coupler-based approaches. For the real ear in-situ approach, a probe microphone is placed in the ear canal and the SPL generated from an audiometric earphone transducer is measured at thresholds and LDLs. Also with the hearing aid in place, the probe microphone measures the aided response SPL to some acoustic input (e.g., rumoring speech, speech-shaped noise etc.). The aided output SPL of the hearing aid can be directly compared to the SPL of the dynamic range of hearing to ensure that aided speech will be audible to the listener. For the second approach, a one-time frequency response SPL measurement is taken in the ear canal using a probe microphone. Another one-time frequency response SPL measurement is taken in a 2-cc coupler. The difference between these two values (known as the real ear to coupler difference; RECD) can be used to transform the hearing aid response SPL measured on a coupler to the real ear response when it is placed in the ear canal of a patient since the unique acoustic signature (transform) is known.

Both the real-ear in-situ and the coupler-based verification procedures for air conduction hearing aids have been shown to be valid and reliable (Scollie & Seewald, 2002) and both procedures allow for direct comparisons of hearing aid output characteristics to the dynamic range of hearing on an individual basis.

Not all individuals can wear air conduction hearing aids. Assuming adequate residual cochlear function, individuals may be candidates for direct bone conduction hearing devices. Typically, a skin penetrating (percutaneous) titanium implant is placed in the parietal-mastoid region of the skull and is used to anchor a direct bone conduction hearing device (see for example the BAHA sold by Cochlear Corp). Despite being clinically available for many years, valid and reliable verification procedures for direct bone conduction hearing aids have not emerged.

State of the Art

Today the verification of direct bone conducting hearing devices typically proceeds in one of two ways: patients are asked about their subjective impressions of the hearing aid volume and sound quality on a "trial and error" basis. With the device connected to a patient and during a conversation with the audiologist, the volume control setting and high/low frequency response parameters are adjusted until the patient claims the device "sounds best" to them. The hearing aid clinician may also adjust the compression settings of the device and ask the patient if they like the sound better after the adjustment. A second approach commonly used for verifying direct bone conducting hearing devices involves measuring aided soundfield thresholds. While aided soundfield thresholds do offer the clinician insight into the softest tones a person can hear in the aided condition, they do little to inform the clinicians about the aided audibility of speech. Moreover, aided soundfield thresholds tell you nothing about the output limits of the device and are known to be unreliable (see Hawkins, 2004; Seewald et al., 1996).

SUMMARY OF THE INVENTION

The present invention offers an approach for relating the amplification characteristics of direct bone conduction hearing devices to the unique dynamic range of hearing in the same units (direct mechanical quantities) at a common reference point. First, hearing thresholds and LDLs are measured using, for example, a direct bone conduction BEST transducer with an accelerometer attached to its rear side and the acceleration levels associated with the dynamic range of hearing are measured directly at the patient's implant (reference point). Also the mechanical output of the direct bone conduction hearing device can be measured directly at the implant by attaching an accelerometer to a BEST transducer and then the device output can be compared directly with the patients hearing LDLs and hearing thresholds. However, alternatively these acceleration level quantities can be converted to equivalent force levels. The reason for this conversion is that the force output of the device can be objectively measured on an artificial skull measuring device. If the dynamic range of hearing can be defined in equivalent force levels, the aided bone conduction hearing device output can be compared directly to the individual's unique auditory characteristics. The hearing device output/frequency response or gain can be manipulated and measured on the artificial skull force measuring device and compared to the auditory dynamic range in order to assess the adequacy of the verification for each device.

In alternative approaches, force levels can be measured directly on the patient by a front mounted force gauge or indirectly by a constant force output transducer.

Although not commercially available yet the present invention is applicable to transcutaneous direct bone conduction devices where the transducer is attached to the bone subcutaneously.

DETAILED DESCRIPTION

Definitions

Direct Bone Conduction Hearing Device:

Direct bone conduction hearing devices are defined as devices where the vibration transducer is rigidly attached to the skull bone without intervening soft tissues. These devices can be either percutaneous (i.e. using a skin penetrating abutment attached to a fixture integrated to the skull bone) or transcutaneous (where at least the driving side of the transducer is attached subcutaneously to the skull bone). Such subcutaneously placed transducers has an outer housing made of titanium.

Sound Pressure Levels (SPL):

When possible the Sound Pressure Level (SPL) is used as the objective measure where the SPL dB is referred to 20μ Pascal.

Acceleration Levels (A):

For bone conduction applications (hearing via the skull bone) Acceleration can be used as the objective measure where the A dB is referred to 1 m/s².

Force Levels (F):

Sometimes the Force is used instead of Acceleration and the F dB is then referred to 1μ Newton.

Hearing Thresholds (HT):

The hearing thresholds are defined as the softest sound a person can hear at each frequency. There are several methods to determine hearing thresholds such as Hughson-Westlake ascending technique. Hearing threshold levels can be measured in several quantities such as SPL, Acceleration ($A_{HT}$) or Force ($F_{HT}$).

Loudness Discomfort Levels (LDL):

The Loudness Discomfort Levels are defined as loudest sound that a person can tolerate at each frequency. There are several procedures to determine LDL such as described by Hodgetts 2007 (thesis). Loudness Discomfort Levels can be measured in several quantities such as SPL, Acceleration ($A_{LDL}$) or Force ($F_{LDL}$).

Mechanical Impedance (Z):

The mechanical impedance is defined by $Z=F/v$ (applied force/response velocity). The velocity is determined by $v=A/jw$ where A is acceleration, j is the complex constant and w is the angular frequency. Using these relations for the same point of attachment the Acceleration levels (A) can be converted to Force levels (F) and vice versa according to $F=A*Z/jw$.

Acceleration Frequency Response Function ($A_{FRF}$):

The acceleration frequency response is defined as the output acceleration from a transducer attached to a certain load divided by the input voltage level to its electrical terminals ($A_{FRF}=A/Vin$). This quotient is determined in each patient for all frequencies of interest.

Force Frequency Response Function ($F_{FRF}$):

The force frequency response is defined as the output force from a transducer attached to an artificial skull force measuring device divided by the input voltage level to its electrical terminals ($F_{FRF}=F/Vin$). This quotient is determined one-time for all frequencies of interest.

Audiometric Transducer:

An audiometric transducer is defined as a transducer that transforms electrical energy to mechanical energy in order to measure a patients hearing thresholds and LDLs to mechanical stimuli. Such a transducer can be of different types like, for example, the BEST but should have the additional feature that it is capable of measuring directly or indirectly the mechanical excitation level at a certain input voltage.

BEST Transducer:

A Balanced Electromagnetic Separation Transducer (BEST) is a transducer principle that is described by Håkansson 2003 and in patents SE Patent No: 0000810-2, SE Patent No: 0201441-3, and SE Patent No: 0600843-7.

Artificial Skull Force Measuring Device:

An artificial skull force measuring device is a device that is capable of objectively measuring the force output from a direct bone conduction hearing device as described for example by Håkansson 1989 or SE patent No: 8502411-5.

Force Gauge:

A force gauge is defined as a measuring device capable of measuring the force at the contact point between the transducer and the implant.

Constant Force Output Transducer:

A constant force output transducer is defined as a transducer designed so that it delivers a constant force output level for a given range of load impedances such as the range of skull impedances among the patients. In other words such a transducer should have an output impedance sufficiently lower than the skull impedances. Such a transducer can be calibrated so that for a given electrical input voltage to the transducer there is a given output force level independent of which patient it is connected to.

Prescription Rule:

A prescription rule is defined as a mathematic algorithm that use the individual patients hearing parameters, such as hearing thresholds and LDLs, to compute an "optimal" (in some sense) mechanical output from a direct bone conduction hearing device for a specific acoustical input.

Acousto-Mechanical Force Targets:

Desired force output from a transducer for a given specific acoustical input to a direct bone conduction device according to some prescription or fitting rule.

DESCRIPTION

In particular the invention relates to a method for fitting and verifying the output of direct bone conduction hearing devices to a patient, which method is characterized in that a. in a first step the hearing threshold and loudness discomfort levels are measured directly on a titanium implant of a patient, b. in a second step these hearing threshold and loudness discomfort levels are converted to equivalent force thresholds ($F_{HT}$) and loudness discomfort levels ($F_{LDL}$) on an artificial skull force measuring device, c. in a final step the output force levels of the direct bone conduction device is measured in a free sound field with the device attached to the said artificial skull force measuring device and compared to the $F_{HT}$ and the $F_{LDL}$ as the base for final adjustments of the device.

In a preferred embodiment the acousto-mechanical force targets are calculated for the hearing device according to a prescription rule and for a certain acoustic input and then the device performance is measured and adjusted to meet the targets.

In a preferred embodiment acceleration thresholds ($A_{HT}$), acceleration loudness discomfort levels ($A_{LDL}$) and acceleration frequency response ($A_{FRF}$) are measured on the said titanium implant of a patient and the force frequency response ($F_{FRF}$) is measured on an artificial skull force measuring device, where after the ratio $F_{FRF}/A_{FRF}$ is calculated and used to convert the $A_{HT}$ and $A_{LDL}$ data to corresponding $F_{HT}$ and $F_{LDL}$ data.

In a preferred embodiment the acceleration thresholds ($A_{HT}$), acceleration loudness discomfort levels ($A_{LDL}$) and acceleration frequency response ($A_{FRF}$) on the patient is measured by an audiometric BEST transducer where an accelerometer is rigidly attached to its rear side.

In a preferred embodiment acceleration thresholds ($A_{HT}$), acceleration loudness discomfort levels ($A_{LDL}$) and acceleration frequency response ($A_{FRF}$) on the patient are measured by an audiometric transducer where an accelerometer is rigidly attached to its front side.

In a preferred embodiment the force threshold and hearing discomfort levels of the patient is measured directly by a force gauge between the transducer and the implant.

In a preferred embodiment force threshold ($F_{HT}$) and loudness discomfort levels ($F_{LDL}$) on the patient are measured indirectly by a constant force output transducer, for example, a specially designed BEST transducer.

In a preferred embodiment force threshold ($F_{HT}$) and loudness discomfort levels ($F_{LDL}$) on the patient are measured indirectly by a BEST transducer acting as a constant force output transducer.

In a preferred embodiment the frequencies of interest are the typical audiometric frequencies.

In a preferred embodiment the frequencies are 125 to 8000 Hz.

In a further aspect of the invention it relates to an apparatus for carrying out the method which apparatus comprises an artificial skull force measuring device, a test station, a loudspeaker, a microphone, an audiometer, and an audiometric transducer.

In a preferred embodiment thereof it further comprises the patients own direct bone conduction hearing device.

A measurement set-up for the current verification procedure.

DETAILED DESCRIPTION OF THE ILLUSTRATED EMBODIMENTS

FIG. 1 shows a set-up for using the present innovation on a patient 1 comprising an artificial skull force measurement device 2, which later on is providing a force signal to a computer based audio test station 3. The computer based audio test station provides a signal to a loudspeaker 4, the sound of which is received by a reference microphone 5 providing a further input signal to the computer based audio test station 3. An audiometer 6 receives and transmits control signals (automatically or manually) from and to the computer based audio test station 3, as well as deliver a voltage signal to the Balanced Electromagnetic Separation Transducer (BEST) 7 which is defined as an audiometric transducer and generates the vibration signal and provides an acceleration signal 8, from an accelerometer 8a attached to its rear central portion, to the computer based audio test station 3. The microphone 5 is placed in close relationship to the microphone of a direct bone conduction hearing device 9 to be fitted to the patient 1, and which excites the artificial skull force measurement device 2. The determination of the patient hearing thresholds and loudness discomfort levels are measured in mechanical quantities on a titanium implant 10 on the patient 1.

In addition, the hearing threshold 11 and LDL 12 are displayed in the audio test station 3 also some hearing device characteristics are measured and displayed like maximum power output (MPO) 13 and noise floor 14. Also the hearing device output 15 at a certain acoustical input can be measured and displayed. By comparing these data a trained audiologist can adjust the device characteristics to improve the hearing rehabilitation in that particular patient.

To be more objective the hearing device output 15 at a certain acoustical input can be compared with some of the acousto-mechanical targets 16 of that input which are determined according to a prescription rule. The device characteristics can then be adjusted to meet the targets for that acoustic input.

FIG. 2 shows an alternative embodiment where the audiometric transducer has a front mounted accelerometer or force gauge 8b.

FIG. 3 shows a further embodiment where the audiometric transducer is designed to be a constant force output transducer 8c where the output force is calibrated in relation to the input voltage level.

The invention claimed is:

1. A method for fitting and verification of direct bone conduction hearing devices, wherein
   a. in a first step the hearing threshold and loudness discomfort levels are measured directly on a titanium implant of a patient,
   b. in a second step these hearing threshold and loudness discomfort levels are converted to equivalent force thresholds ($F_{HT}$) and loudness discomfort levels ($F_{LDL}$) on an artificial skull force measuring device,
   c. in a final step the output force levels of a direct bone conduction hearing device are measured in a free sound field with the device attached to said artificial skull force measuring device and compared to the $F_{HT}$ and the $F_{LDL}$ as the base for final adjustments of the device.

2. The method according to claim 1 wherein acousto-mechanical force targets are calculated for the hearing device according to a prescription rule and for a certain acoustic input and then the device performance is measured and adjusted to meet the targets.

3. The method according to claim 1, wherein acceleration thresholds ($A_{HT}$), acceleration loudness discomfort levels ($A_{LDL}$) and acceleration frequency response ($A_{FRF}$) are measured on the said titanium implant of a patient and the force frequency response ($F_{FRF}$) is measured on an artificial skull force measuring device, where the ratio $F_{FRF}/A_{FRF}$ is calculated and used to convert the $A_{HT}$ and $A_{LDL}$ data to corresponding $F_{HT}$ and $F_{LDL}$ data.

4. The method according to claim 3, wherein the acceleration thresholds ($A_{HT}$), acceleration loudness discomfort levels ($A_{LDL}$) and acceleration frequency response ($A_{FRF}$) on the patient is measured by an audiometric BEST transducer where an accelerometer is rigidly attached to its rear side.

5. The method according to claim 3, wherein acceleration thresholds ($A_{HT}$), acceleration loudness discomfort levels ($A_{LDL}$) and acceleration frequency response ($A_{FRF}$) on the patient are measured by an audiometric transducer where an accelerometer is rigidly attached to its front side.

6. The method according to claim 1, wherein the force threshold and hearing discomfort levels of the patient is measured directly by a force gauge between an audiometric transducer and the implant.

7. The method according to claim 1, wherein force threshold ($F_{HT}$) and loudness discomfort levels ($F_{LDL}$) on the patient are measured indirectly by a constant force output transducer.

8. The method according to claim 7, wherein force threshold ($F_{HT}$) and loudness discomfort levels ($F_{LDL}$) on the patient are measured indirectly by a BEST transducer acting as a constant force output transducer.

9. The method according to claim 3, wherein the frequencies are audiometric frequencies.

10. The method according to claim 9, wherein the frequencies are in the range of 125 to 8000 Hz.

11. An apparatus for carrying out the method according to claim 1, which comprises an artificial skull force measuring device, a test station, a loudspeaker, a microphone, an audiometer, and an audiometric transducer including a sensor or acting as a constant force output transducer.

12. The apparatus according to claim 11, wherein it further comprises a direct bone conduction hearing device.

* * * * *